United States Patent [19]

Strickler

[11] Patent Number: 5,367,085
[45] Date of Patent: Nov. 22, 1994

[54] PREPARATION OF TICL$_3$ COORDINATION COMPLEXES

[75] Inventor: Jamie R. Strickler, Baton Rouge, La.

[73] Assignee: Albemarle Corporation, Richmond, Va.

[21] Appl. No.: 123,666

[22] Filed: Sep. 20, 1993

[51] Int. Cl.$^5$ ........................... C07F 17/00; C07F 3/00
[52] U.S. Cl. ........................................ 549/206; 556/51
[58] Field of Search .......................... 556/51; 549/206

[56] References Cited

PUBLICATIONS

Inorganic Syntheses, vol. 21, 1982, pp. 137–138, Tetrahydrofuran Complexes of Selected Early Transition Metals.

J. Org. Chem. 1989, 54, pp. 3748–3749, An Optimized Procedure for Titanium–Induced Carbonyl Coupling, J. E. McMurry, et al.

*Primary Examiner*—Nicky Chan
*Attorney, Agent, or Firm*—David M. Bunnell

[57] ABSTRACT

TiCl$_3$ coordination complexes with ethers are prepared by adding TiCl$_3 \cdot \frac{1}{3}$AlCl$_3$ to an ether solvent so as to form a solid TiCl$_3$-ether coordination complex in said solvent.

11 Claims, No Drawings

PREPARATION OF TICL₃ COORDINATION COMPLEXES

This invention relates generally to the formation of coordination compounds of titanium and more specifically to the preparation of TiCl₃-ether coordination compounds from TiCl₃.⅓AlCl₃.

Coordination compounds of TiCl₃ such as TiCl₃ complexes with, dimethoxyethane (DME) or tetrahydrofuran (THF) are useful intermediates in forming metallocenes by the reaction of the complexes with cyclopentadienyl containing ligands. The metallocenes, when activated, catalyze olefin polymerization.

It is known to prepare a TiCl₃(THF)₃ complex by refluxing anhydrous tetrahydrofuran with TiCl₃ as reported in Inorganic Synthesis, Vol. 21, 1982, p. 137. The coordination complex TiCl₃(DME)₁.₅ is prepared in an analogous manner as reported in *J. Org. Chem.* 1989, 54, 3748–3749. Pure TiCl₃ starting material can be obtained by hydrogen reduction of TiCl₄, which is costly. Aluminum reduction of TiCl₄ is less expensive but the product is the complex, TiCl₃.⅓AlCl₃ rather than pure TiCl₃. I have now discovered that TiCl₃.⅓AlCl₃ will react with ether solvents at ambient temperature to form solid TiCl₃ coordination complexes in good to high yields and purity. When using cyclical ethers, most, and in some cases virtually all, of the aluminum chloride by-product stays in solution. The process not only provides the advantage of starting with a more readily available and less expensive material compared to starting with pure TlCl₃, but the presence of the aluminum chloride may also be responsible for driving the spontaneous formation of the Ti(III) chloride coordination compounds at ambient temperatures such that reflux of the reaction mixture is not necessary.

In accordance with this invention there is provided a process for preparing a TiCl₃ coordination complex comprising adding TiCl₃.⅓AlCl₃ to an ether solvent so as to form a solid, TiCl₃-ether coordination complex in said solvent.

The starting material TiCl₃.⅓AlCl₃, is obtained by aluminum reduction of TiCl₄, as known in the art, and this material is commercially available in anhydrous form.

Suitable ether solvents are cyclic ethers and acyclic polyethers having from about 4 to 10 carbon atoms. Cyclic ether solvents have the advantage of solvating the AlCl₃. Because the AlCl₃ remains in solution in the ether, a solid, substantially AlCl₃ free TiCl₃-ether coordination complex is produced. Non-limiting examples of ethers include tetrahydrofuran (THF), ethylene glycol dimethyl ether (DME or glyme), 1,4-dioxane, 2-methoxyethyl ether (diglyme), triethylene glycol dimethyl ether, tetrahydropyran, diethylene glycol dimethyl ether, and the like.

The amount of solvent used in the process will generally range from about 10 to 25 mL per gram of TiCl₃.⅓AlCl₃. Preferably, the TiCl₃.⅓AlCl₃ is slowly added to the stirred solvent at ambient temperatures. The reaction is exothermic and the application of external heat is not necessary. Generally, the reaction temperature will vary from about 25° to 60° C. The TiCl₃-ether complex separates as a solid from the reaction mixture and can be recovered by filtration from the solvent—AlCl₃ solution. Surprisingly, when using cyclic ether solvents the amount of AlCl₃ in the product is less than about 500 ppm aluminum (e.g. substantially AlCl₃ free) and, when using 1,4-dioxane, the presence of AlCl₃ was not detected (<1 ppm aluminum).

The invention is further illustrated by, but is not intended to be limited to, the following examples.

EXAMPLE 1

Synthesis of TiCl₃(THF)₃

A 500 mL flask was filled with 200 ml of dry, distilled tetrahydrofuran. The solvent was stirred and 15.1 grams of solid, maroon-red TiCl₃.⅓AlCl₃ were added gradually. A maroon slurry formed and the solution warmed considerably. Almost immediately, blue crystalline solids of TiCl₃(THF)₃ were observed. After stirring for 19 hours, the slurry was filtered on a coarse frit. The blue solids were washed with a 50/50 mixture of THF/Et₂O (50 mL total). The solids were dried in vacuo. The yield was 17.5 grams or 62%. The blue solids were analyzed and shown to contain only 288 ppm of aluminum.

EXAMPLE 2

Synthesis of TiCl₃(THF)₃

A 250 mL flask was filled with 100 ml of dry, distilled tetrahydrofuran. The solvent was stirred and 4.04 grams of maroon-red TiCl₃.⅓AlCl₃ were added gradually. A maroon solution formed and the solution warmed. After a few minutes, blue crystalline solids of TiCl₃(THF)₃ were observed. After stirring overnight, the slurry was filtered on a coarse frit. The blue solids were washed with approximately 20 mL of THF. The solids were dried in vacuo. The yield of blue solids was 2.60 grams or 34%.

EXAMPLE 3

Synthesis of TiCl₃(DME)₁.₅

In a 100 mL flask were placed 50 mL of anhydrous ethylene glycol dimethyl ether (DME or glyme). The solvent was stirred and 3.24 grams of maroon-red TiCl₃.⅓AlCl₃ were added. The reaction immediately ensued and blue solids began to form. The reaction was stirred overnight and then the slurry was filtered on a coarse frit. The solids were washed with 15 mL of DME. The solids were dried in vacuo. The yield of light blue solid TiCl₃(DME)₁.₅ product was 3.79 grams or 80%. These solids contained 1.98% aluminum.

EXAMPLE 4

Synthesis of TiCl₃(1,4-Dioxane)₃

In a 200 mL flask was placed 65 mL of anhydrous 1,4-dioxane. The solvent was stirred and 3.16 grams of maroon-red TiCl₃.⅓AlCl₃ were added. A maroon slurry formed. After approximately 30 minutes, blue-green solids were observed. The reaction was stirred overnight and then the slurry was filtered on a coarse frit. The solids were washed with two 10 mL portions of 1,4-dioxane. The solids were dried in vacuo. The yield of mint-green solid TiCl₃(1,4-Dioxane)₃ product was 5.24 grams or 79%. These solids contained <1 ppm of aluminum.

What is claimed is:

1. A process for preparing a TiCl₃ coordination complex with an ether, said process comprising adding TiCl₃.⅓AlCl₃ to an ether solvent so as to form a solid TiCl₃-ether coordination complex in said solvent, wherein said solvent is selected from the group consisting of cyclic ethers and acyclic polyethers having from 4 to about 10 carbon atoms.

2. The process of claim 1 wherein the ether is selected from the group consisting of tetrahydrofuran, 1,4-dioxane, ethylene glycol dimethyl ether, triethylene glycol dimethyl ether, tetrahydropyran and diethylene glycol dimethyl ether.

3. The process of claim 1 wherein said ether is a cyclic ether and said complex is substantially $AlCl_3$ free.

4. The process of claim 3 wherein said ether is selected from the group consisting of tetrahydrofuran and 1,4-dioxane.

5. The process of claim 1 wherein said ether is an acyclic polyether.

6. The process of claim 5 wherein said ether is ethylene glycol dimethyl ether.

7. The process of claim 1 wherein said $TiCl_3.\frac{1}{3}AlCl_3$ is added at ambient temperature.

8. The process of claim 1 including the step of separating said solid $TiCl_3$-ether coordination complex from the ether solvent solution.

9. The process of claim 7 wherein said complex is $TiCl_3(tetrahydrofuran)_3$.

10. The process of claim 7 wherein said complex is $TiCl_3(ethylene\ glycol\ dimethyl\ ethyl)_{1.5}$.

11. The process of claim 7 wherein said complex is $TiCl_3(1,4-dioxane)_3$.

* * * * *

REEXAMINATION CERTIFICATE (3144th)

United States Patent [19]

Strickler

[11] B1 5,367,085

[45] Certificate Issued Feb. 25, 1997

[54] PREPARATION OF TICL₃ COORDINATION COMPLEXES

[75] Inventor: Jamie R. Strickler, Baton Rouge, La.

[73] Assignee: Albermarle Corporation, Richmond, Va.

Reexamination Request:
No. 90/004,137, Feb. 13, 1996

Reexamination Certificate for:
Patent No.: 5,367,085
Issued: Nov. 22, 1994
Appl. No.: 123,666
Filed: Sep. 20, 1993

[51] Int. Cl.⁶ .............................. C07F 17/00; C07F 3/00
[52] U.S. Cl. .............................................. 549/206; 556/51
[58] Field of Search ............................... 549/206; 556/51

[56] References Cited

U.S. PATENT DOCUMENTS

| | | |
|---|---|---|
| 3,032,511 | 5/1962 | Lander et al. |
| 3,723,403 | 3/1973 | Greaves et al. |
| 3,769,233 | 10/1973 | Hermans et al. |
| 4,085,064 | 4/1978 | Wristers. |
| 4,183,826 | 1/1980 | Ueno et al. |
| 4,210,738 | 7/1980 | Hermans et al. |
| 4,306,047 | 12/1981 | Kortbeek et al. |
| 4,431,569 | 2/1984 | Wristers. |

OTHER PUBLICATIONS

Coutinho, et al., "Influence of the Method of Synthesis on the Properties of TiCl₃," *Eur. Polym. J.* (1992) 28(6):695–698.

"Transition Metal Catalyzed Polymerization Alkenes and Dienes" Roderic P. Quirk, Ed., MMI Press, pp. 71–73 (Published 1981).

*Primary Examiner*—Nicky Chan

[57] ABSTRACT

TiCl₃ coordination complexes with ethers are prepared by adding TiCl₃·⅓AlCl₃ to an ether solvent so as to form a solid TiCl₃-ether coordination complex in said solvent.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 5–8 and 10 are cancelled.

Claims 3, 9 and 11 are determined to be patentable as amended.

Claim 4, dependent on an amended claim, is determined to be patentable.

New claims 12, 13 and 14 are added and determined to be patentable.

3. [The process of claim 1 wherein said ether is a cyclic ether] *A process for preparing a $TiCl_3$ coordination complex with an ether, said process comprising adding maroon-red $TiCl_3.\frac{1}{3}AlCl_3$ to an ether solvent so as to form a solid $TiCl_3$-ether coordination complex in said solvent, wherein said solvent is a cyclic ether having from 4 to about 10 carbon atoms and said complex is substantially $AlCl_3$ free.*

9. The process of claim [7] *3* wherein said $TiCl_3.\frac{1}{3}AlCl_3$ is added at ambient temperature *and* wherein said complex is $TiCl_3(tetrahydrofuran)_3$.

11. The process of claim [7] *3* wherein said $TiCl_3.\frac{1}{3}AlCl_3$ is added at ambient temperature *and* wherein said complex is $TiCl_3(1,4$-dioxane$)_3$.

*12. The process of claim 3 wherein said solid $TiCl_3$-ether coordination complex has a titanium atom to bound oxygen atom ratio of 1:3; wherein the amount of said ether used as solvent is in the range of from about 10 to 25 mL of ether per gram of $TiCl_3.\frac{1}{3}AlCl_3$; and wherein said ether solvent is tetrahydrofuran.*

*13. The process of claim 3 wherein said solid $TiCl_3$-ether coordination complex has a titanium atom to bound oxygen atom ratio of 1:3; wherein the amount of said ether used as solvent is in the range of from about 10 to 25 mL of ether per gram of $TiCl_3.\frac{1}{3}AlCl_3$; and wherein said ether solvent is 1,4-dioxane.*

*14. The process of claim 3 wherein said solid $TiCl_3$-ether coordination complex has a titanium atom to bound oxygen atom ratio of 1:3; wherein the amount of said ether used as solvent is in the range of from about 10 to 25 mL of ether per gram of $TiCl_3.\frac{1}{3}AlCl_3$; wherein said $TiCl_3.\frac{1}{3}AlCl_3$ is added at ambient temperature; wherein said complex is substantially $AlCl_3$ free; and wherein said ether solvent is selected from the group consisting of tetrahydrofuran and 1,4-dioxane.*

* * * * *